US008839661B2

(12) United States Patent
Ortiz et al.

(10) Patent No.: US 8,839,661 B2
(45) Date of Patent: Sep. 23, 2014

(54) DIRECT QUANTITATIVE COLORIMETRIC MEASUREMENT OF LIQUID FOAM

(75) Inventors: Rebecca S. Ortiz, Midland, MI (US); Jeff R. Anderson, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 882 days.

(21) Appl. No.: 12/912,069

(22) Filed: Oct. 26, 2010

(65) Prior Publication Data

US 2012/0096930 A1    Apr. 26, 2012

(51) Int. Cl.
*G01N 13/02*    (2006.01)
*G01N 21/25*    (2006.01)
*G01N 21/78*    (2006.01)
*G01J 3/46*    (2006.01)

(52) U.S. Cl.
CPC ............. *G01N 13/02* (2013.01); *G01N 21/78* (2013.01); *G01N 21/25* (2013.01); *G01N 2013/025* (2013.01)
USPC ........................................ 73/60.11; 356/402

(58) Field of Classification Search
USPC ..................................................... 73/60.11
See application file for complete search history.

(56) References Cited

U.S. PATENT DOCUMENTS

| | | | | |
|---|---|---|---|---|
| 2,315,983 | A * | 4/1943 | Ross et al. | 73/60.11 |
| 2,380,679 | A * | 7/1945 | Smith | 73/60.11 |
| 3,027,755 | A * | 4/1962 | Groll, Jr. et al. | 73/60.11 |
| 3,107,519 | A * | 10/1963 | McGinn | 73/60.11 |
| 3,725,014 | A | 4/1973 | Pestonji et al. | |
| 4,061,016 | A * | 12/1977 | Noel et al. | 73/60.11 |
| 4,084,426 | A * | 4/1978 | Gales | 73/60.11 |
| 4,677,304 | A * | 6/1987 | Camp et al. | 250/577 |
| 5,783,826 | A * | 7/1998 | Meunier | 250/341.8 |
| 5,824,886 | A * | 10/1998 | Selby et al. | 73/60.11 |
| 6,276,613 | B1 | 8/2001 | Kramer | |
| 6,582,505 | B1 | 6/2003 | Bouvy et al. | |
| 6,672,142 | B2 * | 1/2004 | Yasui et al. | 73/60.11 |
| 6,762,212 | B2 | 7/2004 | Oohara et al. | |
| 6,932,330 | B2 | 8/2005 | Fournel et al. | |
| 6,960,617 | B2 | 11/2005 | Omidian et al. | |
| 7,094,127 | B2 | 8/2006 | Radford et al. | |
| 7,442,722 | B2 | 10/2008 | Sui et al. | |
| 7,565,933 | B2 | 7/2009 | Kippie et al. | |
| 2003/0217421 | A1 | 11/2003 | Besel | |
| 2007/0039378 | A1 * | 2/2007 | Wollenberg | 73/53.05 |
| 2007/0185250 | A1 | 8/2007 | Mader et al. | |
| 2008/0166303 | A1 * | 7/2008 | Tamarkin et al. | 424/43 |
| 2008/0223413 | A1 | 9/2008 | Radford | |
| 2010/0069281 | A1 | 3/2010 | Guignot et al. | |

FOREIGN PATENT DOCUMENTS

| | | | | |
|---|---|---|---|---|
| DE | 4036048 | * | 11/1990 | 73/60.11 |
| JP | 11-64225 | * | 3/1999 | |
| WO | WO 96/22343 | * | 7/1996 | |
| WO | 2004053468 | | 6/2004 | |

OTHER PUBLICATIONS

Anderson et al., "Dow Coating Materials—High Throughput Method for Evaluating Foam Stabilization in NOP PUD", 27 Pages, (No Date).
Andersson et al., "Foam II. Chemical defoaming and a method for measuring the effectiveness of antifoaming agents in aqueous dispersions", Faerg och LackScandinavia, 1983, vol. 29 No. 1.
Berger et al., "Analysis and measurement of foaming phenomena in water-based coating systems", Journal of Coatings Technology, 1976, vol. 48 No. 621, pp. 55-59.
Breindel, "RAW Materials: Sugar Coating: Molecular-based defoamer eliminates foam and enhances coating properties", Modern Paint and Coatings, 2000, vol. 90 No. 5, pp. 18-22.
Frank et al., "A small-scale system to evaluate anti-foam performance", ASTM Special Technical Publication, 1985, 50-58.
Karras et al., "Testing of deaeration and defoamer chemicals with an air content meter", Paperi ja Puu—Paper and Timber, 1989, vol. 71 No. 4, pp. 352-354.
Mohler et al., "Accelerating Cellulosic Ether Development Using High Throughput Approaches", Core R&D—New Products, Core R&D—Information Research, Spring ACS 2009, 25 Pages.
Reader et al., "Elimination of surface defects in waterborne coatings", Asia Pacific Coatings Journal, 2006, vol. 19 No. 1, 4 Pages.
Schrickel, "Defoaming agents for water-based coatings: Influences of the defoamer and influences on the defoamer", Royal Society of Chemistry, 1999, 29-47.
Schwartz et al., "Waterborne industrial maintenance primers—performance improvements via an additives approach", Modern Paint and Coatings, 1996, vol. 86 No. 12, pp. 25-28, 30, 32-33.
Wallhorn et al., "Defoamers—nothing but empirical results?" Surface Coatings Australia, 1998, vol. 35 No. 9.
Proglyde DMM Product Information.

* cited by examiner

*Primary Examiner* — Daniel S Larkin
(74) *Attorney, Agent, or Firm* — Karl E. Stauss; Cantor Colburn LLP

(57) ABSTRACT

The present invention generally relates to a foaminess characterization method for characterizing liquid foams and defoamers and a foam generation method for generating the liquid foams.

13 Claims, 4 Drawing Sheets

DIRECT QUANTITATIVE COLORIMETRIC MEASUREMENT OF LIQUID FOAM

BACKGROUND OF THE INVENTION

1. Field of the Invention

The invention generally relates to a foaminess characterization method for characterizing liquid foams and test substances and a foam generation method for generating the liquid foams.

2. Description of Related Art

Industry needs to determine degree of foaminess of liquid foams or defoaming effectiveness of defoamers in liquid foams for diverse applications such as, for example, soaps, detergents, foamable pharmaceutical and cosmetic compositions, paints, and coatings in order to evaluate quality thereof. A common industry measurement for this purpose is foam height of a liquid foam sample in a graduated cylinder. This method typically uses about 75 milliliters (mL) per sample and takes 15 minutes to 20 minutes per sample to measure initial height of foamable liquid in graduated cylinder, transfer foamable liquid to a container and vigorously stir sample therein, transfer stirred sample back to graduated cylinder and measure height of stirred sample. When this physical property measurement works well, foam height of the sample increases in proportion to increasing degree of foaming thereof.

United States Patent Application Publication Number US 2008/0166303 A1 mentions, among other things, a colored or colorable topical composition comprising: a) a foamable base composition comprising, 1) a flowable carrier composition; 2) a color agent; wherein the color agent is effective to impart, increase, or decrease or otherwise affect color of a foam produced from the foamable composition and wherein the color agent is one or more agents selected from the group consisting of a colored active agent, a colored indicator, a colored excipient, a pigment, a dye, a colorant and a coloring agent; b) a propellant at a concentration of about 3% to about 25% by weight of the total composition; wherein the base composition has a first color; and wherein the foam comprising the colored or colorable topical composition has a second color upon dispensing from an aerosol container, and wherein the first color and the second color are visually different. US 2008/0166303 A1 also mentions, among other things, a method of changing color and a use as a diagnostic.

There is a need in the art for an improved method of determining degree of foaminess of liquid foams or defoaming effectiveness of defoamers contained therein.

BRIEF SUMMARY OF THE INVENTION

The inventors discovered that using foam height, cross-sectional area, or volume to measure degree of foaminess of a liquid foam in a test container becomes problematic when size of the test container is small (e.g., less than 5 milliliters), surface tension of the liquid is high such that the liquid foam elevates at container walls, or both. In these cases experimental error leads to unreliable foaminess measurements. The inventors further discovered that employing a color measurement additive (e.g., colorant, dye, or pigment only used to characterize a foam) in a test liquid foam and using a color property to determine degree of foaminess of the test liquid foam can easily confound accurate foaminess measurements. For example, such confounding can be due to the indirect nature of the measurement (i.e., what is being measured is color measurement additive-modified liquid foam, not the liquid foam itself), deleterious changes in chemical composition of the liquid of the test liquid foam due to the characterizing additive (e.g., changes in solubility of the color measurement additive in the liquid over time, or its effects on solubility of another ingredient in the liquid, such as a result of slow dissolution/precipitation kinetics or change in pH of the liquid), foaming or defoaming chemical effects of a characterizing additive (e.g., color measurement additive) or interference with a defoamer's defoaming effect, characterizing additive's interference with ad rem character of other ingredients of the test liquid foam (e.g., color measurement additive's interference with color of other ingredients of the test liquid foam), need for experimentation to discover a specific characterizing additive (e.g., color measurement additive) for a particular test liquid foam, or a combination thereof. The inventors also realized that changes in color due to dissolution or precipitation of a colored substance during or between measurements or changes in color due to thermal degradation of a foam are not measurements of degree of foaminess.

Thus, the inventors desired to discover a method of measuring a physical characteristic of degree of foaminess of test liquid foams per se that is independent of changes in the liquid's chemical composition, turbidity, and any other confounding factor and works with a variety of different liquid compositions and defoamer agents. Naturally, then, they initially sought to avoid characterizing additives (e.g., color measurement additives) and measurements of chemical, mechanical, optical, or thermal properties.

The inventors, however, unexpectedly discovered and describe herein an invention method employing an optical property measurement method that is independently reflective of degree of and quantitatively accurate for determining degree of foaminess of test liquid foams per se and defoaming effectiveness of defoamers therein. Another advantage is the invention measurement is independent of effects of turbidity (i.e., a decreased intensity of light caused by scattering) of the test liquid foam. Still another advantage is their invention method does not require use of a characterizing additive (e.g., color measurement additive) or physical measurement of foam height, cross-sectional area, or volume to accurately determine the degree of foaminess. Thus, the invention method works well whether using large- of small-volume samples and containers, even sample volumes of 0.5 mL and less and container volumes of 1 mL and less. The inventors also provide a method of generating the test liquid foams having small sample volumes in the small-volume containers. The ability to use small sample and container volumes, and the invention foam generating method, especially enable the invention methods to be advantageously used in high throughput workflows. The invention high throughput workflows are especially useful as a means for accelerating materials and formulations research and development, particularly for applications such as soaps, detergents, foamable pharmaceutical and cosmetic compositions, paints, and coatings. The inventors discovered their invention method is useful for independently characterizing foaminess of test liquid foams per se, defoaming effectiveness of defoamers and potential defoamers, or a combination thereof. The inventors further discovered their invention method is useful for characterizing any test substance that can be employed as an ingredient of a test liquid foam, not just the foamable liquid and defoamer.

In a first embodiment the present invention provides a foaminess characterization method comprising determining a quantitative change in degree of foaming of a test liquid foam as a direct quantitative colorimetric function of the test liquid foam.

In a second embodiment the present invention provides a foaminess characterization method comprising determining defoaming effectiveness of a test substance on a foamable liquid as a direct quantitative colorimetric function of degree of foaming of a test liquid foam comprising the foamable liquid and the test substance, wherein the direct quantitative colorimetric function comprises a quantitative change between comparable first and second quantitative color measurements, wherein at least one of the quantitative color measurement is made on the test liquid foam.

In a third embodiment the present invention provides a foam generation method of generating a test liquid foam in a container having a volume of at most 2 milliliters and being dimensioned for containing the test liquid foam, the method comprising mechanically agitating a foamable liquid, a foam-generating effective number of beads, and gaseous atmosphere in the container in such a way so as to surround bubbles of gas of the gaseous atmosphere therewith and generate the test liquid foam in the container.

As used herein, the term "bead" means a particle having sufficient density, shape, and size such that when the particle is disposed in the foamable liquid, mechanical agitation of the disposition would be effective for generating shearing strain on and deforming the foamable liquid. Beads can, but preferably do not, define an aperture therethrough. Preferably, the beads end up in the test liquid foam once mechanical agitation is stopped.

The term "comparable" means admitting of meaningful comparison vis-à-vis the direct quantitative colorimetric function.

The term "color measurement additive" means a material that is effective to impart, increase, or decrease or otherwise affect color of a foam produced from the foamable liquid or preliminary mixture and having a chief function of characterizing the test liquid foam; the material is not native to, and not normally an ingredient of, the test liquid foam, preliminary mixture, or test substance.

The term "container" means a receptacle, which can be open or, preferably, closed. Examples of preferred containers are bottles, flasks, open and capped vials, open and closed wells such as, for example, wells of a typical 96-well plate adapted for use in a high throughput workflow.

The term "defoamer" means a molecule or substance that can be added to a foamable liquid, and is substantially insoluble in the foamable liquid, and functions in such a way so as to inhibit generation of, slow rate of generation of, prevent formation of, reduce size or severity of, or increase rate of dissipation of a liquid foam (referred to herein as test liquid foam) of the foamable liquid, or a combination thereof.

The term "defoaming effectiveness" means degree of inhibiting generation of, slowing rate of generation of, preventing formation of, reducing size or severity of, or increasing rate of dissipation of a liquid foam, or a combination thereof.

The phrase "degree of foaming" means an absolute or relative amount or extent of a physical state comprising a mass of gas bubbles in a matrix comprising mostly, and preferably consisting essentially of, a liquid film.

The term "determining" means ascertaining definitely, as after consideration, investigation, calculation, or a combination thereof.

The term "dimensioned" means sufficiently sized and adequately shaped for an intended use.

The term "direct quantitative colorimetric function" means a result-effective variable analysis, characterization, or determination employing a numerical value for at least one color parameter that was measured directly from, or derived from a direct measurement made on, the test liquid foam lacking the color measurement additive. The term "color parameter" means a measurable or calculable quality of light having a wavelength of from 400 nanometers (nm) to 750 nm.

The term "foamable liquid" means a non-gaseous, non-vaporous fluid material capable of serving as a matrix film for gas bubbles, the material comprising a solvent, a solution comprising the solvent and a solute dissolved therein, or a suspension comprising a finely-divided particulate solid widely dispersed in the solvent or solution.

The phrase "foam-generating effective number" means a quantity sufficient to produce shearing strain on, and deformation of, the foamable liquid after 30 seconds of vigorous mechanical agitation, preferably as described later.

The term "foaminess characterization" means a description of at least one distinguishing quality or trait of liquid foam.

The term "gaseous atmosphere" means a non-liquid, non-solid, non-plasma environment comprising at least one gas or a mixture comprising the at least one gas and at least one vapor.

The phrases "generating a liquid foam" and "generate a liquid foam" respectively mean producing or produce a physical state comprising a mass of gas bubbles in a matrix comprising mostly, and preferably consisting essentially of, a non-gaseous, non-vaporous fluid film (i.e., a liquid film).

The term "liquid foam" means a physical state comprising a mass of gas bubbles in a matrix comprising mostly, and preferably consisting essentially of, a non-gaseous, non-vaporous fluid film (i.e., a liquid film); liquid foam is not a solid foam (e.g., not a polyurethane foam).

Preferably, the aforementioned physical state comprising the aforementioned mass of bubbles is spontaneously reversible such that substantially all of the mass of bubbles is spontaneously collapsible under force of gravity.

The phrase "made on" as used herein with "the test liquid foam" and the like means with and dependent upon measuring a quality of.

The term "mechanically agitating" means moving by applying a physical motive force in such a way so as to generate shearing strain on and deform the foamable liquid; mechanically agitating is not a chemical, electrical, or electromagnetic motive force.

The term "quantitative color measurement" means an ascertained numerical value for a color parameter, wherein the ascertained numerical value can be a measured quantity, a statistical quantity (e.g., a mean, median, or the like of a plurality of measured quantities), or a quantity mathematically derived from the measured or statistical quantity; not a qualitative measurement (e.g., not darker or lighter or deeper color or lighter color).

The term "quantitative change" means any mathematical way of making a numerical comparison between two numbers that is suitable for the invention. For example, obtain (e.g., calculate, compute, or determine) the quantitative change as a mathematical function of at least two quantitative color measurements.

The term "test substance" means a finely-divided solid particulate or liquid material that can be dissolved, suspended, or both in the foamable liquid.

The term "test liquid foam" means a liquid foam as defined above, wherein foaminess of the liquid foam is capable of being characterized by at least one of the invention foaminess characterization methods, and, preferably, lacks the color measurement additive.

The invention foaminess characterization methods independently are reflective of, and quantitatively accurate for determining a, degree of foaminess of test liquid foams per se. Such invention foaminess characterization methods advantageously measure a characteristic of degree of foaminess of the test liquid foam per se, that is, such invention methods are effective without requiring, and in some embodiments lack, a characterizing additive (e.g., color measurement additive) in the test liquid foam. Such invention foaminess characterization methods are quantitatively accurate and are valuable for determining defoaming effectiveness of defoamers contained in the test liquid foams. Another advantage is the invention foaminess characterization methods are useful with, and in some embodiments employ, test liquid foams that are transparent, translucent, or opaque (i.e., turbid). Still another advantage is that such invention foaminess characterization methods do not require use of, and in some embodiments exclude, a physical measurement of foam height, cross-sectional area, or volume, which physical measurements are problematic with small sample and container volumes. Such invention foaminess characterization methods are effective for quantitatively determining the degree of foaminess whether using, and in some embodiments use, large- or small-volume samples and containers, even enable invention embodiments employing sample volumes of 0.5 mL and less and container volumes of 1 mL and less. Compatibly with such invention foaminess characterization methods, the invention foam generation method advantageously enables generation of, and in some embodiments generates, the test liquid foams having small sample volumes in the small-volume containers. The ability to use small sample and container volumes makes the invention foam generation method and foaminess characterization methods especially enabling for, and especially advantageous for use in, and in some embodiments employ, high throughput workflows. High throughput workflows preferably employ small sample and container volumes so as to minimize sample amounts and maximize throughput thereof. All invention methods enable throughput increase, and in some embodiments maximization, in the foaminess characterization and defoamer evaluation art. All invention methods are useful for characterizing foaminess of test liquid foams whether foaming is desired (e.g., soaps and pharmaceutical foams) or not desired (e.g., paints and coatings), and in some embodiments foaming is desired and in other embodiments foaming is not desired. All invention methods, including the invention high throughput workflows, are especially useful as a means for enabling and accelerating foamable materials and formulations research and development, particularly for applications such as, and in some embodiments the invention methods employ, soaps, detergents, foamable pharmaceutical and cosmetic compositions, paints, and coatings.

Additional embodiments are described in accompanying drawing(s) and the remainder of the specification, including the claims.

BRIEF DESCRIPTION OF THE DRAWING(S)

Some embodiments of the present invention are described herein in relation to the accompanying drawing(s), which will at least assist in illustrating various features of the embodiments.

Figure 3A:
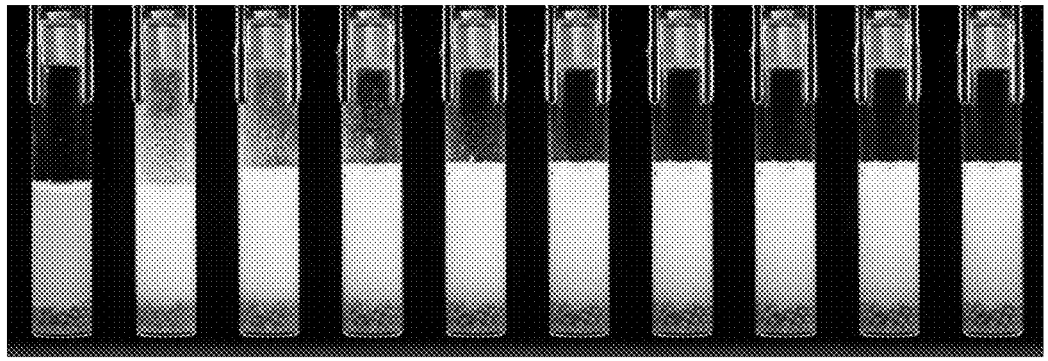
Figure 3B:
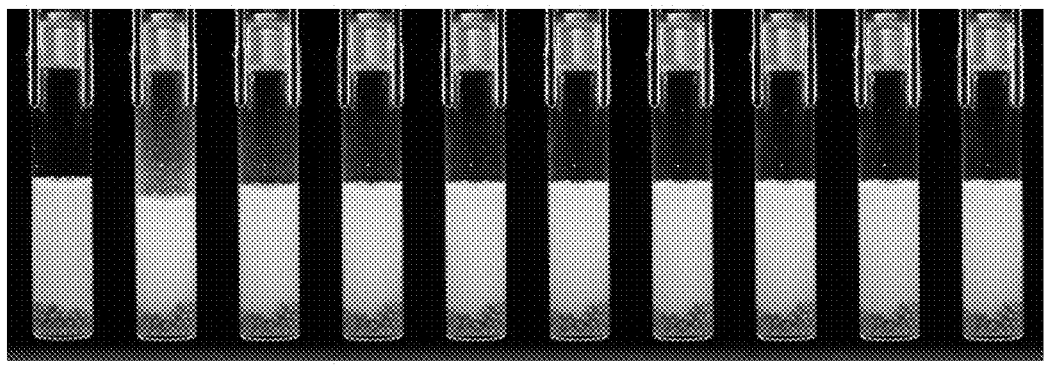
Figure 3C:
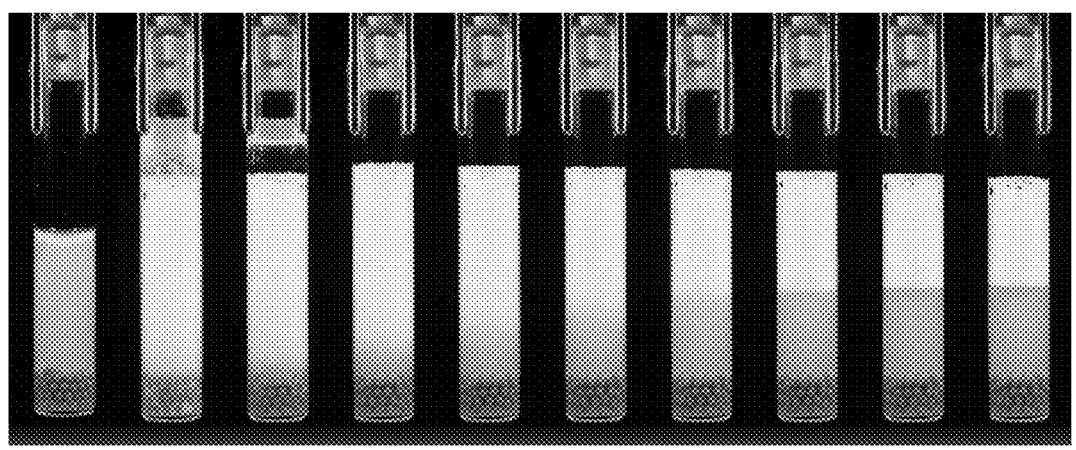

FIGS. 3a to 3c respectively show, from left-to-right in each, test liquid foam samples after shaking for 15 seconds as described in Examples 4 to 13, 14 to 23, and 24 to 33, respectively.

Figures 4A, 4B, 4C, 4D:
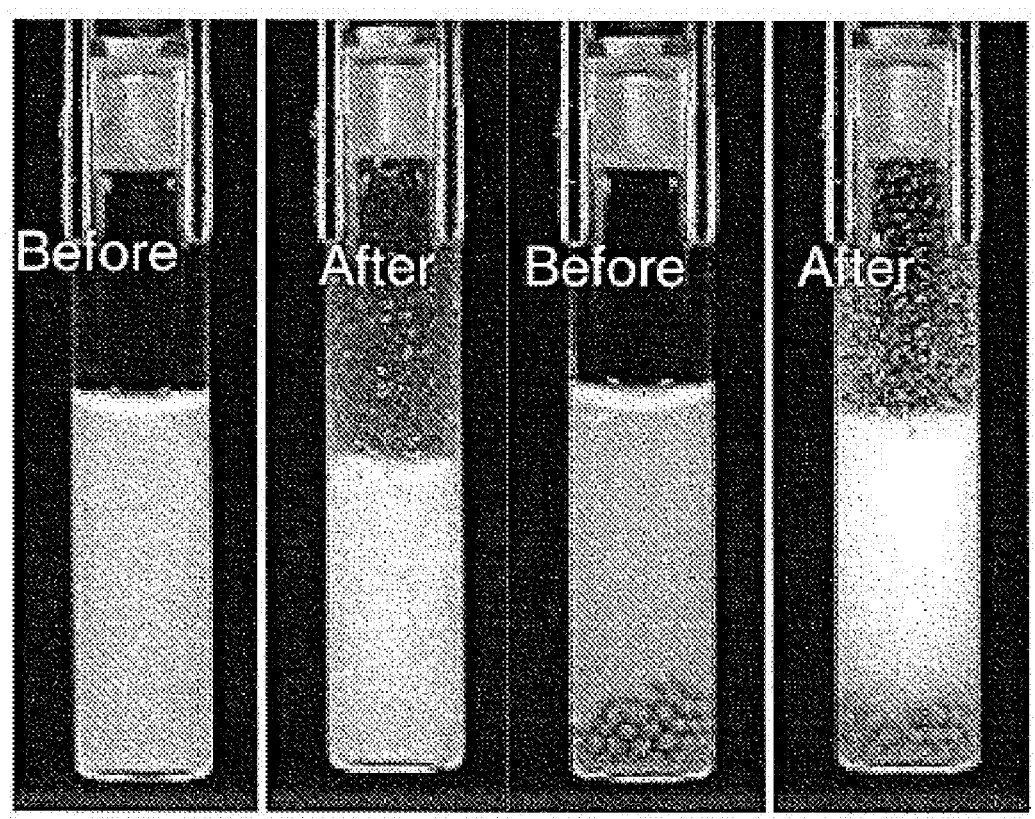

FIGS. 4a to 4d show before-and-after comparisons without beads in non-invention Comparative Example A and showing foam-generating effect with beads in invention Example A (FIGS. 4c and 4d).

DETAILED DESCRIPTION OF THE INVENTION

The invention relates to the foaminess characterization method for characterizing liquid foams or test substances and the foam generation method for generating the liquid foams, as summarized previously. Preferably, the test substances are compounds or materials that are characterized by the invention foaminess characterization method as being a defoamer.

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Summary or Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, any lower limit of a range of numbers, or any preferred lower limit of the range, may be combined with any upper limit of the range, or any preferred upper limit of the range, to define a preferred aspect or embodiment of the range. Unless otherwise indicated, each range of numbers includes all numbers, both rational and irrational numbers, subsumed within that range (e.g., the range from about 1 to about 5 includes, for example, 1, 1.5, 2, 2.75, 3, 3.80, 4, and 5).

The word "optionally" means "with or without." For example, "optionally, an additive" means with or without an additive.

In an event where there is a conflict between a compound name and its structure, the structure controls.

In an event where there is a conflict between a unit value that is recited without parentheses, e.g., 2 inches, and a corresponding unit value that is parenthetically recited, e.g., (5 centimeters), the unit value recited without parentheses controls.

As used herein, "a," "an," and "the," are used following an open-ended term such as comprising to mean "at least one." In any aspect or embodiment of the instant invention described herein, the term "about" in a phrase referring to a numerical value may be deleted from the phrase to give another aspect or embodiment of the instant invention. In the former aspects or embodiments employing the term "about," meaning of "about" can be construed from context of its use. Preferably "about" means from 90 percent to 100 percent of the numerical value, from 100 percent to 110 percent of the numerical value, or from 90 percent to 110 percent of the numerical value. In any aspect or embodiment of the instant invention described herein, the open-ended terms "comprising," "comprises," and the like (which are synonymous with "including," "having," and "characterized by") may be replaced by the respective partially closed phrases "consisting essentially of," "consists essentially of," and the like or the respective closed phrases "consisting of," "consists of," and the like to give another aspect or embodiment of the instant invention. The partially closed phrases such as "consisting essentially of" and the like limits scope of a claim to materials or steps recited therein and those that do not materially affect the basic and novel characteristic(s) of the claimed invention. The term "characterizable" is open-ended and means distinguishable, if desired, and preferably means is distinguished as described.

In the present application, when referring to a preceding list of elements (e.g., ingredients), the phrases "mixture thereof," "combination thereof," and the like mean any of at least two, including all, of the listed elements. The term "or" used in a listing of members, unless stated otherwise, refers to the listed members individually as well as in any combination, and supports additional embodiments reciting any one of the individual members (e.g., in an embodiment reciting the phrase "at least 10 percent," the "at least" supports another embodiment reciting "10 percent" and still another embodiment reciting "more than 10 percent."). The term "plurality" means at least two, wherein each plurality is independently selected unless indicated otherwise. The term "independently" means separately without regard for another. The terms "first," "second," et cetera serve as a convenient means of distinguishing between at least two elements or limitations (e.g., a first chair and a second chair) and do not imply quantity or order unless specifically so indicated. The symbols "≤" and "≥" respectively mean less than or equal to and greater than or equal to. The symbols "<" and ">" respectively mean less than and greater than. The term "characterizable" means capable of being distinguished, if desired.

Where the invention, or a portion thereof (e.g., element or step), is defined in the alternative by a Markush group having at least two members, the invention contemplates preferred embodiments too numerous to recite each one herein. For convenience, such preferred embodiments can be readily determined by: (i) selecting any single member from the Markush group, thereby limiting scope of the Markush group to the selected single member thereof; or (ii) deleting any single member from the Markush group, thereby limiting the Markush group to any one of the remaining member(s) thereof. In some embodiments the member that is selected or deleted is based on one of the Examples or other species of the present invention described herein.

In some embodiments the method of the first embodiment comprises determining a quantitative change in degree of foaming of the test liquid foam and a comparable unfoamed foamable liquid as a direct quantitative colorimetric function comprising a first quantitative color measurement made on the test liquid foam and a second quantitative color measurement made on the comparable unfoamed foamable liquid. As used herein, the term "unfoamed" means substantially lacking or completely lacking gas bubbles (gas-bubble free), wherein "substantially lacking gas bubbles" and "substantially gas bubble free" are synonymous and mean volume of the foamable liquid that is gas bubble free is at most 5 percent greater than volume of entirely gas-bubble free foamable liquid.

In some embodiments the method of the first embodiment comprises determining a quantitative change in degree of foaming of the test liquid foam and a comparable liquid foam as a direct quantitative colorimetric function comprising a first quantitative color measurement made on the test liquid foam and a second quantitative color measurement made on the comparable liquid foam.

In some embodiments the method of the first embodiment comprises a quantitative change in degree of foaming of the test liquid foam and a heuristic degree of foaming thereof expressed as the direct quantitative colorimetric function comprising a first quantitative color measurement made on the test liquid foam. As used herein, the term "heuristic" means a common sense expectation based on experimental datum or data from a comparable, non-identical liquid foam. Examples of comparable, non-identical liquid foams are experimentally tested foams having same chemical composition as test liquid foam but where on of the ingredients of the foam is present therein to a known greater or lesser extent and experimentally tested foams wherein one of the ingredients of the test liquid foam other than the foamable liquid is lacking or is replaced by an ingredient having a comparable chemical structure and being in the experimentally tested foam at a concentration comparable to that of the ingredient being replaced thereby in the test liquid foam.

In some embodiments of the method of the first or second embodiment, the first quantitative color measurement is made on the foamable liquid or a preliminary mixture comprising the foamable liquid and the test substance; and the second quantitative color measurement is made on the test liquid foam soon after the test liquid foam has been generated from the preliminary mixture such that the second quantitative color measurement reflects an initial degree of foaminess of the test liquid foam. Preferably, the preliminary mixture is substantially gas bubble-free i.e., substantially unfoamed; the direct quantitative colorimetric function reflects defoaming effectiveness of the test substance on inhibiting liquid foam formation. The term "soon after" means a period of time allowing at most a 1% loss of foaminess or, preferably, one minute.

In some embodiments the method of the first or second embodiment comprises:

Illuminating a substantially gas bubble-free preliminary mixture by light in such a way so as to obtain an operatively illuminated preliminary mixture that is substantially gas bubble-free;

In a first measuring step, quantitatively measuring color of the operatively illuminated preliminary mixture to give the first quantitative color measurement;

Removing the illumination and mechanically agitating the preliminary mixture under foam-generating conditions so as to generate the test liquid foam;

Soon after the mechanically agitating step, illuminating the test liquid foam by light in such a way so as to obtain an operatively illuminated test liquid foam;

In a second measuring step, quantitatively measuring color of the operatively illuminated test liquid foam to give the second quantitative color measurement, wherein the first and second quantitative color measurements are comparable to each other;

Obtaining the quantitative change as a mathematical function of the first and second quantitative color measurements; and Evaluating the defoaming effectiveness of the test substance as the direct quantitative colorimetric function of the degree of foaming of the test liquid foam based on the quantitative change that is the mathematical function of the first and second quantitative color measurements, wherein a smaller absolute value for the quantitative change in color of the test liquid foam indicates a greater degree of defoaming effectiveness of the test substance and a larger absolute value for the quantitative change in color of the test liquid foam indicates a lesser degree of defoaming effectiveness of the test substance.

The illuminating steps are included herein for any embodiments wherein other at least one of the other steps of the invention method is carried out in absence of light or in presence of light that is less desirable for the quantitatively measuring color. The term "operatively illuminated" means exposed to light so as to enable the quantitatively measuring color.

In some embodiments the method of the first or second embodiment further comprises:

Waiting for a period of time after the second measuring step to give a standing test liquid foam;

After the period of time and in a third measuring step, quantitatively measuring a color of an operatively illuminated standing test liquid foam to give a third quantitative color measurement of the test liquid foam, wherein the third and second quantitative color measurements are comparable to each other;

Obtaining the quantitative change as a mathematical function of the third and second quantitative color measurements; and Further evaluating the defoaming effectiveness of the test substance as the direct quantitative colorimetric function of the degree of foaming of the test liquid foam based on the quantitative change that is the mathematical function of the third and second quantitative color measurements, wherein a smaller absolute value for the quantitative change in color of the test liquid foam indicates a greater degree of defoaming effectiveness of the test substance and a larger absolute value for the quantitative change in color of the test liquid foam indicates a lesser degree of defoaming effectiveness of the test substance.

The waiting period of time can vary depending upon the particular circumstances of the invention method. Examples of the particular circumstances that can affect the waiting period of time are temperature, defoaming effectiveness of a test substance, particular chemical composition and concentration of ingredients of the test liquid foam, and degree of mechanical agitation experienced by the preliminary mixture to give the test liquid foam. Determining a suitable waiting period of time is within ordinary skill in the art. Examples of a range of a suitable waiting period of time are from 10 seconds to 30 days, and preferably from 1 minute to 60 minutes.

In some embodiments of the method of the first or second embodiment, the first quantitative color measurement is made on the test liquid foam soon after the test liquid foam has been generated from a preliminary mixture comprising the foamable liquid and the test substance such that the first quantitative color measurement reflects an initial degree of foaminess of the test liquid foam; and the method further comprises allowing the test liquid foam to stand for a period of time to give a standing test liquid foam before the second quantitative color measurement is made on the standing test liquid foam. Preferably, the direct quantitative colorimetric function thus reflects defoaming effectiveness of the test substance on a standing liquid foam over time.

In some embodiments the method of the first or second embodiment comprises:

Mechanically agitating a substantially gas bubble-free preliminary mixture under foam-generating conditions to generate the test liquid foam;

Soon after the mechanically agitating step, illuminating the test liquid foam by light in such a way so as to obtain an operatively illuminated test liquid foam;

In a first measuring step, quantitatively measuring a color of the operatively illuminated test liquid foam to give the first quantitative color measurement of the test liquid foam;

Removing the illumination and waiting for a period of time after the first measuring step to give a standing test liquid foam;

Soon after the period of time, illuminating the standing test liquid foam by light in such a way so as to obtain another operatively illuminated test liquid foam;

Quantitatively measuring a color of the other operatively illuminated test liquid foam to give the second quantitative color measurement, wherein the first and second quantitative color measurements are comparable to each other;

Obtaining the quantitative change as a mathematical function of the first and second quantitative color measurements; and Evaluating the defoaming effectiveness of the test substance as the direct quantitative colorimetric function of the degree of foaming of the test liquid foam based on the quantitative change that is the mathematical function of the first and second quantitative color measurements, wherein a smaller absolute value for the quantitative change in color of the test liquid foam indicates a greater degree of defoaming effectiveness of the test substance and a larger absolute value for the quantitative change in color of the test liquid foam indicates a lesser degree of defoaming effectiveness of the test substance.

In some embodiments of the method of the first or second embodiment, the test liquid foam is generated by mechanically agitating the preliminary mixture with a foam-generating effective number of beads and gaseous atmosphere in a container in such a way so as to surround bubbles of gas of the gaseous atmosphere therewith and generate the test liquid foam in the container, which is substantially transparent and substantially colorless and is dimensioned for holding the test liquid foam. Preferably, the direct quantitative colorimetric function of the degree of foaming means that it is a function other than foam height, foam area, or foam volume.

In some embodiments of the method of the first or second embodiment, the method comprises the evaluating step comprising characterizing the test substance as being a defoamer, and the defoamer is a liquid or particulate solid (i.e., powder).

The term "evaluating" means comparing against desired characterization criterion or criteria. Preferably, any invention foaminess characterization method comprises the obtaining step and evaluating step. More preferably, any invention foaminess characterization method further comprises a selecting at least one test substance step. Preferably, the at least one test substance that is selected is a defoamer. Once selected, the selected test substance can be optimally formulated with the foamable liquid and any other ingredient thereof so as to give a composition useful in any one of the applications (e.g., paint or coatings) described herein.

In some embodiments of the method of the first or second embodiment, the direct quantitative colorimetric function comprises quantitative color measurements of a color parameter that is hue, intensity, lightness, luminance, or a combination of at least two color parameters thereof. Preferably, the color parameter is hue, intensity, lightness, luminance, or a combination of at least two color parameters thereof.

In some embodiments of the method of the first or second embodiment, the quantitative measurements are represented in a Commission Internationale de L'Eclairage (CIE) L*a*b* color model. The Commission Internationale de L'Eclairage (CIE) (International Commission on Illumination), an organization that has its central bureau at Kegelgasse 27, 1030 Vienna, AUSTRIA, is a worldwide source of information on all matters relating to the science and art of light and lighting, color, vision, photobiology, and image technology. CIE provides the widely used L*a*b* color model.

In some embodiments of the method of the first or second embodiment, the test liquid foam lacks a color measurement additive selected from the group consisting of a colored active agent, a colored indicator, a colored excipient, a pigment, a dye, a colorant and a coloring agent.

Any foamable liquid can be used in the invention. Preferably the foamable liquid comprises water as a dispersion medium and a finely divided solid or liquid widely distributed therein. Examples of preferred foamable liquids are polymer dispersions, polymer emulsions, and preferably organic polymer dispersions and organic polymer emulsions. An example of the polymer dispersion is a latex paint, aqueous polyurethane dispersion, epoxy dispersion, and aqueous polyolefin dispersion. An example of the polymer emulsion is an acrylic emulsion such as an aqueous poly(acrylic acid) and poly(methacrylic acid) emulsion and an styrene acrylic emulsion such as a poly(styrene acrylic acid) emulsion.

Examples of test substances that can be characterized as such according to the invention foaminess characterization method are carriers, color agents, diluents, excipients, flavorants, surfactants, and defoamers. Preferably, the test substance comprises from about 0.1 weight percent (wt %) to 10 wt % of the test liquid foam. Preferably the defoamer comprises from 0.1 wt % to 5 wt %, and in some embodiments from 0.2 wt % to 2 wt % (e.g., 1.5 wt %). The wt % values are based on total weight of the test liquid foam or, preferably, weight of the foamable test liquid without the defoamer.

Examples of defoamers that can be characterized as such according to the invention foaminess characterization method are oil-based defoamers, powder defoamers, water-based defoamers, silicone-based defoamers, poly(ethylene glycol)- and poly(propylene glycol)-based defoamers, and alkyl polyacrylates. Examples of useful oil-based defoamers are mineral, vegetable, or white oil-based defoamers), preferably also containing a wax or silica to boost performance thereof. Examples of the wax are fatty alcohols, alkali or alkaline metal salts of fatty acid anions, and fatty acid esters. The term "fatty" means ($C_{12}$-$C_{60}$) carbon chains. Examples of powder defoamers are oil-based defoamers coated on a particulate solid carrier such as, for example, silica. Examples of water-based defoamers are vegetable or white oils or the waxes dispersed in water (e.g., dispersed in form of a finely-divided liquid). Examples of the silicone-based defoamers are a silicone oil coating silica particles. Examples of alkyl polyacrylates are poly(methyl methacrylates). Two defoamer examples are TEGO™ Airex 902W or Byk 028 defoamer (described later).

Defoaming effectiveness can be expressed in any useful way such as, for example, (a) to (d): (a) prevention or extent of inhibition of generation of the test liquid foam compared to a heuristically expected size thereof for a particular quantity of foamable liquid, wherein prevention indicates 100 percent (%) defoaming effectiveness and the greater the inhibition (e.g., percent inhibition), the greater the defoamer effectiveness; (b) extent of reduction of size of the test liquid foam after a period of time compared to an initially obtained size thereof, wherein the greater the reduction of size, the greater the defoamer effectiveness; (c) extent of reduction in size of the test liquid foam compared to an initially obtained size thereof per unit amount (e.g., weight or moles) of the test substance being tested as a possible defoamer, wherein the greater the reduction of size per unit amount, the greater the defoamer effectiveness; and (d) rate of reduction of size of the test liquid foam, wherein the greater the rate of reduction of size, the greater the defoamer effectiveness.

A preferred gas of the gaseous atmosphere is air, argon gas, carbon dioxide gas, helium gas, ($C_1$-$C_4$)alkane gas, ($C_2$-$C_4$) alkene gas, nitrogen gas, oxygen gas, ($C_1$-$C_4$)perfluoroalkane gas, ($C_2$-$C_4$)perfluoroalkene gas, an anhydrous form of any one of the preceding gases, or a mixture thereof. A more preferred gas of the gaseous atmosphere is air, argon gas, carbon dioxide gas, helium gas, nitrogen gas, an anhydrous form of any one of the preceding gases, or a mixture thereof, and still more preferred is air, nitrogen gas, an anhydrous form of any one of the preceding gases, or a mixture thereof. In some embodiments of the method of the first or second embodiment, the gaseous atmosphere consists essentially of air.

Examples of useful mechanical agitation methods are purging with a purge gas, rocking, rolling, rotating, shaking, stirring (e.g., with a magnetic stir bar or impeller), tumbling, and a combination thereof. Preferred is rocking, rolling, rotating, shaking, tumbling, or a combination thereof.

Preferably, the test liquid foam lacks the color measurement additive, and more preferably lacks the color measurement additive and any color agent such as a dye, pigment, or other substance having a chief function of imparting color. The color measurement additive is at least one agent selected from the group consisting of a colored active agent, a colored indicator, a colored excipient, a pigment, a dye, a colorant and a coloring agent.

In some embodiments of the method of the first or second embodiment, the container defines a volume of at most 2 milliliters. Such containers are especially useful in high throughput workflows.

In some embodiments each of the foaminess characterization and foam generation methods independently comprises a high throughput workflow. The term "workflow" means an integrated process comprising steps of experimental design, mixing at least two materials together to give test liquid foams, independently measuring quantitative color measurements on the test liquid foams so as to determine at least one direct quantitative colorimetric functions thereof (e.g., degree of foaming), and collecting data from the resulting measurements. In this context, the term "high throughput workflow" means the steps of the workflow are integrated and time-compressed such that an overall time to execute the integrated process of the high throughput workflow is from at least 2.0 times (e.g., at least 10, 50 or 100 times) faster than an overall time to execute a corresponding process of a standard non-high throughput workflow. In some embodiments the foaminess characterization method comprises the high throughput workflow comprising evaluating defoaming effectiveness of a plurality of test substances in a different one of a plurality of test liquid foams, wherein each test liquid foam independently is the same as or different than another test liquid foam; each test substance independently is the same as or different than another test substance. Examples of sources of a difference between test substances are composition, quantity, and combinations thereof. In some embodiments the foam generation method comprises the high throughput workflow comprising providing a plurality of containers, each container being dimensioned for containing the test liquid foam and independently containing a foamable liquid, a foam-generating effective number of beads, and gaseous atmosphere; and mechanically agitating the containers in such a way so as to surround bubbles of gas of the gaseous atmosphere therewith and generate a test liquid foam in each container.

Examples of simple mathematical ways of making a numerical comparison between two numbers that is suitable for the invention are subtraction (numerical difference) and division (numerical ratio) between the at least two quantitative color measurements. The particular order of subtraction or division and sign of the numerical difference are not critical to the invention foaminess characterization methods, which contemplate, for example, subtracting the first quantitative color measurement from the second one, or vice versa, and dividing the second quantitative color measurement change by the first one, or vice versa. More preferably, the mathematical way uses L*a*b* color model and the color change (delta E) mathematical function as determined by equation (EQ 1) described later.

In some embodiments the method of the first or second embodiment further comprises dividing a difference between the first and second quantitative color measurements, or a difference between the second and third quantitative color measurements, or both, by the period of time therebetween so as to obtain a rate of change of the comparable quantitative color measurements of the test liquid foam. In some embodiments the method further comprises determining a rate of change in delta E over time (e.g., time between two quantitative color measurements).

Materials and Methods

Obtain zirconium beads catalog no. 1.0 millimeter (mm) to 1.2 mm diameter ZIRCONOX®, rare earth stabilized tetragonal zirconia polycrystal ceramic from Jyoti Ceramic Industries, Pvt Ltd, Nashik, Maharashtra, India.

Foamable liquids are an aqueous polyurethane (PU) dispersion from The Dow Chemical Company, Midland, Mich., USA. The PU of the PU dispersion is prepared by copolymerizing an aliphatic isocyanate and a natural oil-based polyester polyol. The PU dispersion is approximately 36 wt % PU solids; 20 wt % PROGLYDE™ DMM glycol diether, a propylene oxide-based solvent having a major isomer of $CH_3OCH_2CH(CH_3)OCH_2CH(CH_3)OCH_3$; and the balance water.

Defoamers TEGO™ Airex 902W, TEGO™ Foamex 822, or Byk 028 defoamer. TEGO™ Airex 902W and Foamex 822 defoamers are aqueous emulsions of a polyether siloxane copolymer containing fumed silica and is commercially available from Evonik Tego Chemie GmbH, Essen, Germany. Byk 028 defoamer is an aqueous mixture of polysiloxanes and hydrophobic solids in polyglycol and is commercially available from BYK-Chemie GmbH, Wesel, Germany.

The particular materials used in the below Methods and Examples are not important to the invention methods.

High Throughput Workflow Procedure (A)

Employ a parent sample preparation robot (e.g., Hamilton MICROLAB® STAR robot (Hamilton Company, Reno, Nev., USA), which prepares a plurality of parent preliminary mixtures, daughters 0.5 mL of each parent preliminary mixture into a different 1-mL volume transparent, colorless glass vial disposed in an 8×12 array; manually add a foam-generating effective number of beads (e.g., zirconium beads) to each vial to give daughter preliminary mixtures disposed in the vials; record an initial digital image of each of the daughter preliminary mixtures; shake each of the daughter preliminary mixtures for 30 seconds using a wrist shaker robot to give shaken daughter preliminary mixtures comprising test liquid foams; record a subsequent digital image of each of the test liquid foams; repeat digital imaging step at 1 minute intervals for a total of 10 minutes so as to give a shaken and imaged daughter preliminary mixtures. If desired, allow shaken and imaged daughter preliminary mixtures to stand unshaken for an additional ten minutes and repeat subsequent digital imaging step at 1 minute intervals as to monitor collapse of the test liquid foams over the additional 10 minutes (20 minutes total).

Each sample (e.g., preliminary mixture or test liquid foam) when it is digitally imaged is illuminated with a light-emitting diode (LED) light source. An example of a suitable LED light-emitting device is an LED light bar model LL6212, high intensity line lights, from Advanced Illumination Inc., Rochester, Vt., USA. Examples of suitable ring-shaped white light-emitting device is a ring light Model 6 CFVI, 17 watt circular fluorescent light from StockerYale Inc., Salem, N.H., USA.

The digital images are captured as digital image measurement data with a digital camera and recorded in electronic format with MatLab Image Processing Toolbox software version 5.3 (R2006b) (MathWorks, Inc., Natick, Mass., USA) on a computer readable storage medium. The term "digital image" means a light-based depiction of a substance in an electronically readable and displayable format. The terms "capture" and "record" as applied to digital image means fixing the light-based depiction of the substance in the electronically readable and displayable format. The term "digital camera" means a device for recording the digital image in the electronically readable format (e.g., a computer readable format). Examples of digital cameras include digital "snapshot" recorders and video recorders. Once captured or recorded the digital image can be processed analogically or digitally. Examples of suitable digital cameras are Canon Rebel XT, Nikon D-series and Sony video cameras.

Identify a representative region-of-interest (ROI) area. The ROI can theoretically be any dimension suitable under the circumstances. A useful ROI for 1-mL vials is, typically, 1 millimeter (mm) wide×10 mm tall of the 1-mL vials and will be the same for all vials in a comparison group, i.e., a group containing test samples to be compared with each other (e.g., for all or subset of test liquid foam samples and for all or subset of preliminary mixture test samples). For all samples within a same comparison group, extract the recorded digital image measurement data for each ROI as a subset of such data, and process the convert the extracted ROI measurement data into the CIE L*a*b* color model so as to obtain L*, a*, and b* data for each ROI. For all pixels of data for L*, a*, and b*, perform a statistical analysis of the L*, a*, and b* data to obtain at least one type of statistical data indicating color change, wherein the at least one type of statistical data indicating color change comprises at least one of standard deviation, mean, median, minimum, or maximum value therefor. Store the statistical data in Excel™ (Microsoft Corporation, Redmond, Wash., USA). Calculate CIE L*a*b* color model-based color changes using Equation (EQ 1):

$$\text{Color change (delta } E) = ((L^*_i - L^*_f)^2 + (a^*_i - a^*_f)^2 + (b^*_i - b^*_f)^2)^{1/2} \quad \text{(EQ 1)}$$

wherein: $L^*_i$ is initial lightness; $L_f$ is final lightness; $a_i$ is initial redness-greenness; $a_f$ is final redness-greenness; $b_i$ is initial blueness-yellowness; and $b_f$ is final blueness-yellowness. The term "initial" means before agitation. The term "final" means after agitation. The term "lightness" means a value on a color scale between absolute black and absolute white. The term "redness-greenness" means a value on a red-green color scale. The term "blueness-yellowness" means a value on a blue-yellow color scale.

Compare the statistical data for test samples within a same comparison group (e.g., test liquid foam in the comparison group to quantitatively determine foaminess of different test samples thereof; the test substance comparison group to defoaming effectiveness of different test samples thereof; or the preliminary mixtures comparison group to determine baselines of different test samples thereof. The comparison of the statistical data comprises determining a quantitative change in at least one type of the statistical data, which quantitative change is the instant quantitative change as described herein. Preferably, select at least one test liquid foam as having an acceptable foaminess, at least one test substance as being a defoamer, or both.

Any comparative example(s) provided herein is provided as a contrast to certain embodiments of the present invention and is not meant to be construed as being either prior art or representative of non-invention examples.

Non-limiting examples of the present invention are described below that illustrate some specific embodiments and aforementioned advantages of the present invention. Preferred embodiments of the present invention incorporate one limitation, and more preferably any two, limitations of the Examples, which limitations thereby serve as a basis for amending claims.

EXAMPLE(S) OF THE PRESENT INVENTION

Examples 1 to 3

Figure 1A:
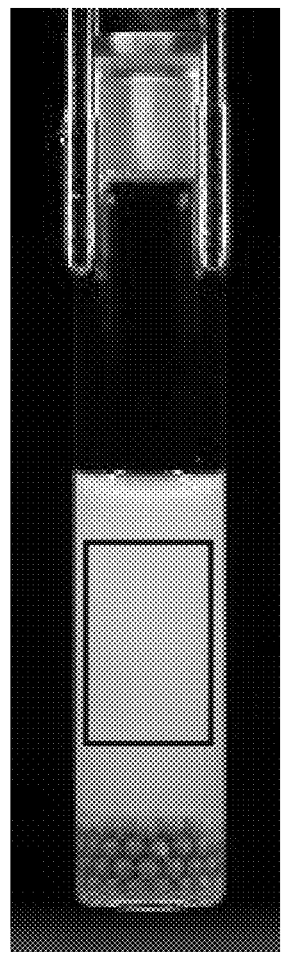
FIGS. 1a and 1b show test liquid foam formulation before shaking (FIG. 1a) and two minutes after shaking (FIG. 1b) as described in Example 1.
Figure 1B:
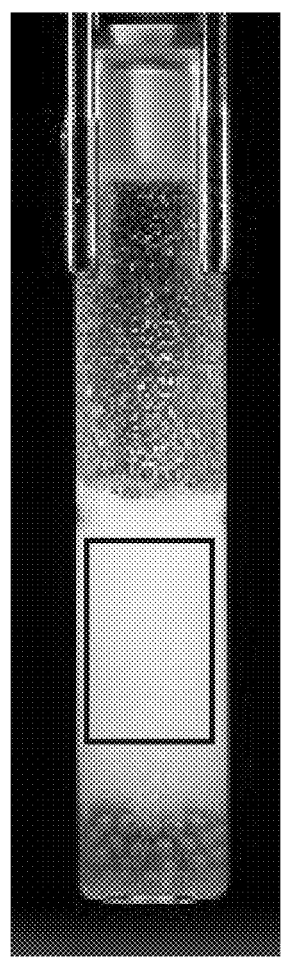
Figure 2:
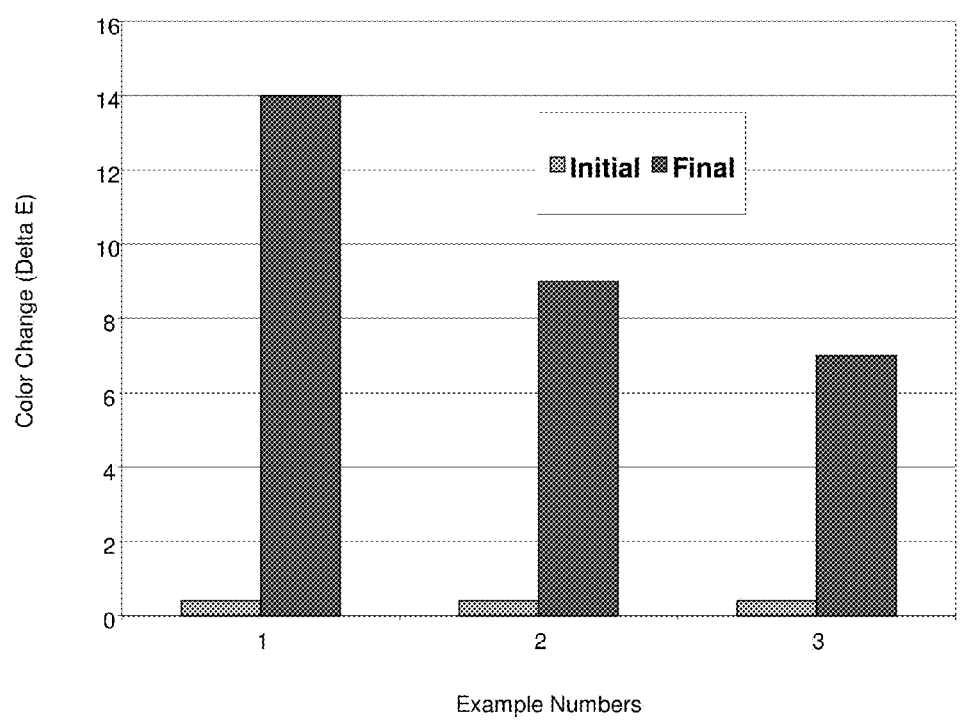
FIG. 2 shows color change (delta E) for Examples 1 to 3 before shaking (short bars, left-hand sides) and after shaking (tall bars, right-hand sides).

Use High Throughput Workflow Procedure (A) with a foamable liquid that is an aqueous polyurethane (PU) dispersion and test substances that are Byk 028 defoamer, and select ROI as illustrated in FIGS. 1a and 1b to give color change data (delta E) for Examples 1 to 3. The Byk 028 defoamer is 1.25 wt % in the PU dispersion based on weight of PU plus water. FIGS. 1a and 1b show test liquid foam formulation before shaking (FIG. 1a) and two minutes after shaking (FIG. 1b) as described in Example 1. FIG. 2 shows color change (delta E) for Examples 1 to 3 before shaking (short bars, left-hand sides) and after shaking (tall bars, right-hand sides).

Examples 4 to 33

Use High Throughput Workflow Procedure (A) with a foamable liquid that is an aqueous polyurethane dispersion containing either test substances that are (combination of TEGO Airex 902W and TEGO Foamex 822, 1:1) or Byk 028 defoamer (FIGS. 3a and 3b) or no test substance (FIG. 3c), and select ROI in a manner similar to that illustrated in FIGS. 1a and 1b to give color change data (delta E) for Examples 4 to 33. Examples 4 to 13 contain 0.5 wt % Byk 028 defoamer in the PU dispersion based on weight of PU plus water. Digital color images of vials of Examples 4 to 13 are shown in FIG. 3a. Examples 14 to 23 contain 0.5 wt % (TEGO Airex 902W and TEGO Foamex 822, 1:1) defoamers in the PU dispersion based on weight of PU plus water. Digital color images of vials of Examples 14 to 23 are shown in FIG. 3b. Examples 24 to 33 contain no defoamer. Digital color images of vials of Examples 24 to 33 are shown in FIG. 3c.

FIGS. 3a to 3c respectively show, from left-to-right in each, test liquid foam samples after shaking for 30 seconds as described in Examples 4 to 13, 14 to 23, and 24 to 33, respectively.

Example A

Use High Throughput Workflow Procedure (A) without beads and with a foamable liquid that is an aqueous polyurethane dispersion containing 0.5 wt % TEGO 902W in the PU dispersion based on weight of PU plus water, and ZIRCONOX® beads. Select ROI in a manner similar to that illustrated in FIGS. 1a and 1b to give color change data (delta E) for Example A.

For comparison purposes, in a non-invention Comparative Example A repeat Example A except without the beads.

FIGS. 4a to 4d show before-and-after comparisons without beads in non-invention Comparative Example A and showing foam-generating effect with beads in Example A (FIGS. 4c and 4d).

As shown by the Examples, the invention foaminess characterization methods independently are reflective of, and quantitatively accurate for determining a, degree of foaminess of test liquid foams per se. Such invention foaminess characterization methods advantageously measure a characteristic of degree of foaminess of the test liquid foam per se, that is, such invention methods are effective without requiring, and in some embodiments lack, a characterizing additive (e.g., color measurement additive) in the test liquid foam. Such invention foaminess characterization methods are quantitatively accurate and are valuable for determining defoaming effectiveness of defoamers contained in the test liquid foams. Another advantage is the invention foaminess characterization methods are useful with, and in some embodiments employ, test liquid foams that are transparent, translucent, or opaque (i.e., turbid). Still another advantage is that such invention foaminess characterization methods do not require use of, and in some embodiments exclude, a physical measurement of foam height, cross-sectional area, or volume, which physical measurements are problematic with small sample and container volumes. Such invention foaminess characterization methods are effective for quantitatively determining the degree of foaminess whether using, and in some embodiments use, large- or small-volume samples and containers, even enable invention embodiments employing sample volumes of 0.5 mL and less and container volumes of 1 mL and less. Compatibly with such invention foaminess characterization methods, the invention foam generation method advantageously enables generation of, and in some embodiments generates, the test liquid foams having small sample volumes in the small-volume containers. The ability to use small sample and container volumes makes the invention foam generation method and foaminess characterization methods especially enabling for, and especially advantageous for use in, and in some embodiments employ, high throughput workflows. High throughput workflows preferably employ small sample and container volumes so as to minimize sample amounts and maximize throughput thereof. All invention methods enable throughput increase, and in some embodiments maximization, in the foaminess characterization and defoamer evaluation art. All invention methods are useful for characterizing foaminess of test liquid foams whether foaming is desired (e.g., soaps and pharmaceutical foams) or not desired (e.g., paints and coatings), and in some embodiments foaming is desired and in other embodiments foaming is not desired. All invention methods, including the invention high throughput workflows, are especially useful as a means for enabling and accelerating foamable materials and formulations research and development, particularly for applications such as, and in some embodiments the invention methods employ, soaps, detergents, foamable pharmaceutical and cosmetic compositions, paints, and coatings.

While the present invention has been described above according to its preferred aspects or embodiments, it can be modified within the spirit and scope of this disclosure. This application is therefore intended to cover any variations, uses, or adaptations of the present invention using the general principles disclosed herein. Further, the application is intended to cover such departures from the present disclosure as come within the known or customary practice in the art to which this present invention pertains and which fall within the limits of the following claims.

What is claimed is:

1. A foaminess characterization method comprising:
providing a substantially gas bubble-free preliminary mixture comprising a foamable liquid and a test substance;
illuminating the substantially gas bubble-free preliminary mixture using a light source in such a way so as to obtain an operatively illuminated preliminary mixture that is substantially gas bubble-free;
in a first measuring step, obtaining a first digital image of the operatively illuminated preliminary mixture with a digital camera and quantitatively measuring color of the operatively illuminated preliminary mixture from the first digital image using a microprocessor programmed to provide quantitative color measurements from digital images to give the first quantitative color measurement;
removing the light source and mechanically agitating the preliminary mixture under foam-generating conditions so as to generate a test liquid foam;
illuminating the test liquid foam using the light source in such a way so as to obtain an operatively illuminated test liquid foam;
in a second measuring step, obtaining a second digital image of the operatively illuminated test liquid foam with a digital camera and quantitatively measuring color of the operatively illuminated test liquid foam from the second digital image using the microprocessor programmed to provide quantitative color measurements from digital images to give a second quantitative color measurement, wherein the first and second quantitative color measurements are comparable to each other;
calculating a quantitative change as a mathematical function of the first and second quantitative color measurements using the microprocessor; and
evaluating defoaming effectiveness of the test substance as the direct quantitative colorimetric function of the degree of foaming of the test liquid foam based on the quantitative change that is the mathematical function of the first and second quantitative color measurements, wherein a smaller absolute value for the quantitative change in color of the test liquid foam indicates a greater degree of defoaming effectiveness of the test substance and a larger absolute value for the quantitative change in color of the test liquid foam indicates a lesser degree of defoaming effectiveness of the test substance.

2. The method as in claim 1, wherein the second quantitative color measurement reflects an initial degree of foaminess of the test liquid foam.

3. The method as in claim 1, the method further comprising:
waiting for a period of time after the second measuring step to give a standing test liquid foam;
after the period of time and in a third measuring step, obtaining a third digital image of the standing test liquid foam with a digital camera and quantitatively measuring a color of the operatively illuminated standing test liquid foam from the third digital image using the microprocessor programmed to provide quantitative color measurements from digital images to give a third quantitative color measurement of the standing test liquid foam, wherein the third and second quantitative color measurements are comparable to each other;
calculating a quantitative change as a mathematical function of the third and second quantitative color measurements using the microprocessor; and
further evaluating the defoaming effectiveness of the test substance as the direct quantitative colorimetric function of the degree of foaming of the test liquid foam based on the quantitative change that is the mathematical function of the third and second quantitative color measurements, wherein a smaller absolute value for the quantitative change in color of the test liquid foam indicates a greater degree of defoaming effectiveness of the test substance and a larger absolute value for the quantitative change in color of the test liquid foam indicates a lesser degree of defoaming effectiveness of the test substance.

4. The method as in claim 3, the method further comprising dividing a difference between the second and third quantitative color measurements by the period of time there between so as to obtain a rate of change of the comparable quantitative color measurements of the test liquid foam and the standing test liquid foam.

5. The method as in claim 1, wherein the test liquid foam is generated by mechanically agitating the preliminary mixture with a foam-generating effective number of beads and gaseous atmosphere in a container in such a way so as to surround bubbles of gas of the gaseous atmosphere therewith and generate the test liquid foam in the container, which is substantially transparent and substantially colorless and is dimensioned for holding the test liquid foam.

6. The method as in claim 5, wherein the container defines a volume of at most 2 milliliters.

7. The method as in claim 5, wherein the gaseous atmosphere consists essentially of air.

8. The method as in claim 1, the method comprising characterizing the test substance as being a defoamer, and the defoamer is a liquid or particulate solid.

9. The method as in claim 1, wherein the quantitative color measurements are expressed as hue, intensity, lightness, luminance, or a combination of at least two of these color parameters.

10. The method as in claim 1, wherein the quantitative color measurements are expressed in a Commission Internationale de L'Eclairage (CIE) L*a*b* color model and the quantitative change is a color change (delta E) calculated according to Equation 1 (EQ 1):

$$\text{Color change (delta }E) = ((L^*_i - L^*_f)^2 + (a^*_i - a^*_f)^2 + (b^*_i - b^*_f)^2)^{1/2} \quad \text{(EQ 1)}$$

wherein: $L^*_i$ is initial lightness; $L_f$ is final lightness; $a_i$ is initial redness-greenness; $a_f$ is final redness-greenness; $b_i$ is initial blueness-yellowness; and $b_f$ is final blueness-yellowness.

11. The method as in claim 1, wherein the test liquid foam lacks a color measurement additive selected from the group consisting of a colored active agent, a colored indicator, a colored excipient, a pigment, a dye, a colorant and a coloring agent.

12. The method as in claim 1, the method further comprising a high throughput workflow.

13. A foaminess characterization method comprising:
providing a substantially gas bubble-free preliminary mixture comprising a foamable liquid and a test substance;
mechanically agitating the substantially gas bubble-free preliminary mixture under foam-generating conditions to generate a test liquid foam;
illuminating the test liquid foam using a light source in such a way so as to obtain an operatively illuminated test liquid foam;
in a first measuring step, obtaining a first digital image of the operatively illuminated first test liquid foam with a digital camera and quantitatively measuring a color of the operatively illuminated test liquid foam from the first digital image using a microprocessor programmed to provide quantitative color measurements from digital images to give a first quantitative color measurement of the test liquid foam;

removing the light source and waiting for a period of time after the first measuring step to give a standing test liquid foam;

illuminating the standing test liquid foam using the light source in such a way so as to obtain an operatively illuminated standing test liquid foam;

in a second measuring step, obtaining a second digital image of the operatively illuminated standing test liquid foam with a digital camera and quantitatively measuring a color of the operatively illuminated standing test liquid foam to give a second quantitative color measurement, wherein the first and second quantitative color measurements are comparable to each other;

calculating a quantitative change as a mathematical function of the first and second quantitative color measurements using the microprocessor; and evaluating defoaming effectiveness of the test substance as the direct quantitative colorimetric function of the degree of foaming of the test liquid foam based on the quantitative change that is the mathematical function of the first and second quantitative color measurements, wherein a smaller absolute value for the quantitative change in color of the test liquid foam indicates a greater degree of defoaming effectiveness of the test substance and a larger absolute value for the quantitative change in color of the test liquid foam indicates a lesser degree of defoaming effectiveness of the test substance.

* * * * *